(12) United States Patent
Ludwig et al.

(10) Patent No.: US 8,690,129 B2
(45) Date of Patent: Apr. 8, 2014

(54) DISPOSABLE MIXING VESSEL

(75) Inventors: Jens Ludwig, Juehnde (DE);
Oscar-Werner Reif, Hanover (DE);
Gerhard Greller, Goettingen (DE);
Wolfgang Kahlert, Koerle (DE);
Guenther Pradel, Goettingen (DE);
Michael Bates, Gloucestershire (GB);
Magail Barbaroux, La Destrousse (FR);
Stephane Baud, La Bouilladise (FR);
Isabelle Gay, Peypin (FR); Sebastian Chaussin, Aubagne (FR)

(73) Assignee: Sartorius Stedim Biotech GmbH (DE)

( * ) Notice: Subject to any disclaimer, the term of this patent is extended or adjusted under 35 U.S.C. 154(b) by 882 days.

(21) Appl. No.: 12/921,407

(22) PCT Filed: Mar. 18, 2009

(86) PCT No.: PCT/IB2009/006077
§ 371 (c)(1),
(2), (4) Date: Sep. 8, 2010

(87) PCT Pub. No.: WO2009/122310
PCT Pub. Date: Oct. 8, 2009

(65) Prior Publication Data
US 2011/0013474 A1 Jan. 20, 2011

Related U.S. Application Data

(60) Provisional application No. 61/069,977, filed on Mar. 19, 2008.

(51) Int. Cl.
*B01F 3/04* (2006.01)

(52) U.S. Cl.
USPC ............ 261/84; 261/93; 261/121.1; 366/273

(58) Field of Classification Search
USPC ................ 261/84, 91, 93, 121.1, 122.1, 124; 366/273
See application file for complete search history.

(56) References Cited

U.S. PATENT DOCUMENTS

| 4,209,259 A | 6/1980 | Rains et al. |
| 4,483,623 A * | 11/1984 | Eaton et al. .................. 366/247 |
| 4,993,841 A | 2/1991 | Lofgren et al. |
| 5,160,461 A * | 11/1992 | Burrows .................... 261/140.1 |

(Continued)

FOREIGN PATENT DOCUMENTS

| DE | 20 2007 005 868 | 8/2007 |
| EP | 1 884 561 | 2/2008 |

(Continued)

OTHER PUBLICATIONS

International Preliminary Report on Patentability, Sep. 30, 2010.

*Primary Examiner* — Charles Bushey
(74) *Attorney, Agent, or Firm* — Gerald E. Hespos; Michael J. Porco; Matthew T. Hespos

(57) ABSTRACT

A disposable mixing vessel comprising a flexible container, a centrally disposed shaft having first and second ends with one or more impellers thereon and a magnetic element associated with a first shaft end, a first flange adapted to rotatably engage the first shaft end and a second flange adapted to rotatably engage the second shaft end.

34 Claims, 13 Drawing Sheets

(56) References Cited

U.S. PATENT DOCUMENTS

| | | | |
|---|---|---|---|
| 5,167,449 A | 12/1992 | Killough | |
| 5,470,152 A | 11/1995 | Rains | |
| 5,727,878 A * | 3/1998 | Sullivan, Jr. | 366/247 |
| 7,481,572 B2 | 1/2009 | Terentiev | |
| 2002/0105856 A1 * | 8/2002 | Terentiev | 366/262 |
| 2005/0181499 A1 | 8/2005 | Brahmbhatt | |
| 2006/0092761 A1 * | 5/2006 | Terentiev | 366/274 |
| 2006/0280028 A1 | 12/2006 | West et al. | |
| 2007/0253288 A1 * | 11/2007 | Mennenga et al. | 366/274 |
| 2008/0131957 A1 * | 6/2008 | Ryan et al. | 435/289.1 |
| 2008/0233631 A1 | 9/2008 | Higashiyama | |
| 2009/0142827 A1 | 6/2009 | Schoeb | |
| 2011/0013473 A1 * | 1/2011 | Ludwig et al. | 366/101 |
| 2011/0058447 A1 * | 3/2011 | Reif et al. | 366/249 |
| 2012/0003733 A1 * | 1/2012 | Gueneron | 435/289.1 |
| 2013/0121103 A1 * | 5/2013 | Castillo et al. | 366/273 |

FOREIGN PATENT DOCUMENTS

| | | |
|---|---|---|
| EP | 2 065 085 | 6/2009 |
| JP | 56-45752 | 4/1981 |
| JP | 1-130722 | 5/1989 |
| WO | 2005/118771 | 12/2005 |
| WO | 2008/088371 | 7/2008 |

* cited by examiner

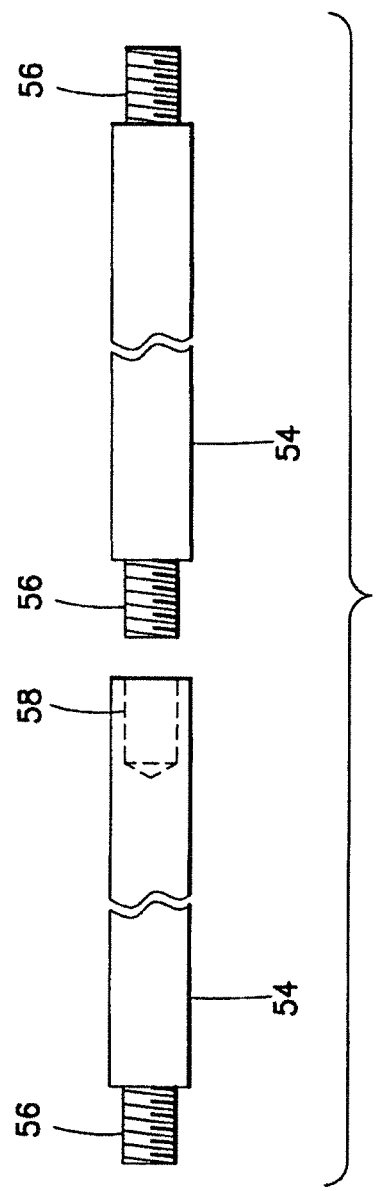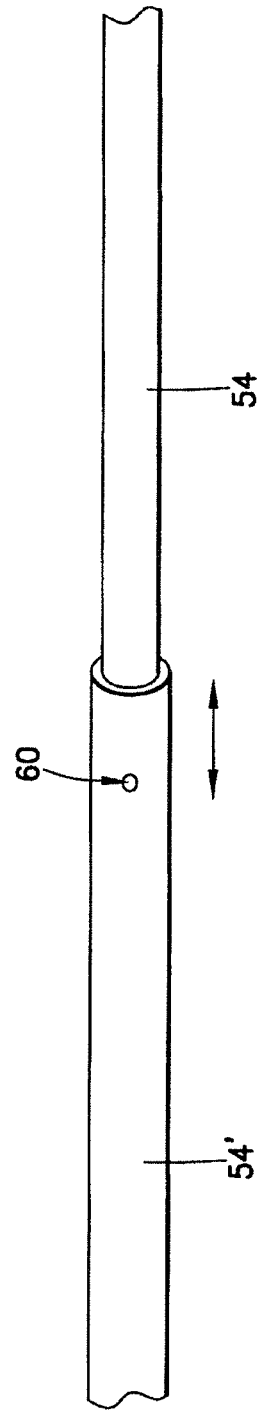
FIG.3A
FIG.3B

DISPOSABLE MIXING VESSEL

REFERENCE TO RELATED APPLICATION

The present application claims priority to U.S. Provisional Patent Application No. 61/069,977, filed on Mar. 19, 2008.

FIELD OF THE INVENTION

The present invention relates to the field of disposable mixing vessels and, more particularly, to a disposable mixing vessel having self-contained, magnetically coupled mixing apparatus included within the mixing vessel as a unit.

BACKGROUND OF THE INVENTION

Agitator or mixing tanks with rotating agitator apparatus are typically used to mix chemical compounds. Frequently, the ingredients being mixed in the agitator tanks require a sterile environment, such as when ingredients are being mixed to prepare a pharmaceutical product. Although some applications do not require a sterile environment, the United States Food and Drug Administration has set out strict sterile requirements for some solutions. To provide such a sterile environment, mixing tanks must be constructed to prevent contaminants from entering the tank during the entire batch process, including filling the tank, mixing and draining the tank.

The use of magnetic drives for driving the agitator apparatus has been known for a long time, since such drives do not require a physical connection or seals between moving parts of the drive means and the agitator apparatus in the sterile environment. In agitator tanks adapted for magnetically driven agitator apparatus, the agitator apparatus within the tank includes a magnetic element near the bottom of the agitator tank, which is engaged by a corresponding magnetic element on a drive motor positioned outside the tank. Activation of the drive motor having the corresponding magnetic element positioned adjacent the magnetic element of the agitator apparatus causes the agitator apparatus to rotate within the agitator tank.

Even more recently, sterile agitator tanks have been developed that utilize a flexible vessel as the mixing container. The flexible vessels can be constructed in a sterile environment and sealed prior to use. Such systems, which use a tank support to maintain the integrity of the flexible container when filled, generally are disposed of after use, to obviate the need for cleaning so as to recreate a sterile environment in the vessel between uses. Thus, the ability to control the sterile environment is greatly improved.

Additionally, agitator tanks for use in sterile applications are known to include the agitator apparatus within the sealed vessel when shipped. In these agitator tanks, the sterile agitator apparatus is placed within the sterile vessel prior to sealing, minimizing the potential for breaching the sterile environment.

Examples of agitator tanks with magnetically driven internal fluid agitating apparatus include U.S. Pat. Nos. 4,209,259; 4,993,841; and 5,470,152, Japanese Patent No. JP 56-045752 and Published PCT Application No. PCT/US02/31478. Each of these references describes agitator tanks with agitating apparatus having driven magnetic elements that are engaged by adjacent cooperating drive magnetic elements associated with a drive means.

Of the references cited, U.S. Pat. No. 5,470,152 describes an agitator tank with a drive housing into which the drive magnet is inserted. An impeller having a magnetic element is attached to the drive housing with the magnetic element having magnets oriented vertically, so that the magnets are parallel with the longitudinal axis of the drive housing containing the cooperating magnetic element of the drive motor. As shown and described in the reference, the impeller is removably attached to the bottom portion of the drive housing with a clip.

U.S. Pat. Nos. 4,209,259 and 4,993,841 describe mixing vessels with magnetically driven agitator apparatus, in the form of impellers mounted on posts in the vessels. Each of these references describe the agitator apparatus as located within the vessel in an area related to a flange or recess that positions the impeller with respect to the drive means. However, the impellers of these references merely reside in the vessel at a single location on a post, and can be removed by pulling on a ring on the terminal end of the agitator apparatus.

Similarly, the device of PCT Application No. PCT/US02/31478 utilizes an impeller that is received by a post located on a rigid portion of the mixing vessel. The remaining portion of the mixing vessel is called out as being a flexible portion, described in the reference as a bag. The impeller has a magnetic element that is driven by an external drive motor having a magnetic drive element.

Japanese Patent No. JP 56-045752 is directed to a magnetically driven stirring device having a rotating circular plate on ball bearings fixed to the bottom of the vessel, where the magnetic element of the agitator apparatus is associated with the bottom of the vessel. The agitator apparatus of this reference is formed of a metal alloy for wear purposes.

None of the prior art references, however, describes a sterile sealed single use mixing vessel including a centrally disposed shaft, attached to the top and bottom portions of the vessel and utilizing radial or thrust bearings, such as slide bearings, ball bearings, journal bearings, or roller bearings, to facilitate rotation of the shaft, on which one or more impellers are mounted. Moreover, none of the references describes a single use mixing vessel having a drain port incorporated into the bottom shaft attachment member for draining the vessel once the mixing process has been completed.

Furthermore, none of the prior art references describes a sterile sealed single use mixing vessel comprising a flexible bag including a centrally disposed shaft, which is attached to the top and bottom portions of the vessel, has one or more impellers, is foldable or may be assembled from sections, whereby the impeller(s) are positioned at a predetermined level. Assembling the centrally disposed shaft may be accomplished from the outside of the mixing vessel by a manual manipulation of the user.

SUMMARY OF THE INVENTION

The present invention is generally directed to a single use mixing vessel comprising a flexible container having a centrally disposed shaft with a magnetic element at one end and one or more impellers mounted thereon, the shaft being associated with top and bottom flanges with radial or thrust bearings, such as slide bearings, ball bearings, journal bearings, or roller bearings, therebetween for facilitating rotation of the shaft, the bottom flange including a drain port with access to the interior of the vessel for draining the vessel. In a preferred embodiment the drain port has a barbed tip, where the tip flares down to a lesser diameter at the terminal end for receiving a harvest line tube.

The mixing vessel preferably also includes one or more inlets for filling the vessel with the materials to be mixed and, optionally, one or more sensors and/or sampling lines for measuring properties of the material in the vessel and/or removing a portion of the material in the vessel for analysis.

In a preferred embodiment, the mixing vessel also includes a sparger for introducing gases into the mixture. When such a sparger is included, the present mixing vessel includes a gas inlet and gas exhaust as well as an internal sparging line to direct the gas to the sparger, which is preferably located at the bottom of the mixing vessel about at least a portion of the bottom flange with which the bottom of the shaft is associated. The sparger line preferably enters the vessel at the top portion and is attached to a side wall, bringing the gas to the sparger at the bottom of the vessel, either through the use of bands or straps that are preferably formed of the material of the interior of the vessel, or as a sleeve of the material attached along the side wall of the vessel.

It is intended that the mixing vessel is constructed so as to create a sterile environment within the vessel, including all of the component parts therein. The mixing vessel can be evacuated of unnecessary gases, hermetically sealed and packed to improve shipping and storage at a facility where the vessel is to be used. Although the preferred embodiment described relates to a sterile environment for mixing materials, there may be circumstances where a sterile environment is not necessary for the mixture and a non-sterile environment is acceptable. Therefore, the present invention is not limited to the maintenance of a sterile environment in the mixing vessel.

In a preferred embodiment, packing for shipping and storage may be improved through the use of a sectioned, foldable or telescopic shaft, thus reducing the size of the mixing vessel prior to use. Such an embodiment is especially preferred when the mixing vessel is intended for large volume applications.

The vessel may be formed in any suitable geometry, size or shape, however, it is preferably constructed to have a cylindrical shape with substantially hemispherical top and bottom. In this regard, it is intended that the vessel will be placed into a rigid or semi-rigid tank generally conforming to the geometry, size and/or shape of the vessel for structural integrity prior to, during and after filling with the materials to be mixed. Of course, manufacturing methods for the vessel may vary, depending on the shape desired and the tolerances sustainable.

It was a surprise to find that the flexible container can be operated up to volumes of more than 100 liters without separate outer stabilizing apparatuses. The reason for this is the double mounting of both ends of the central shaft on both a first and a second flange. Moreover, this construction makes it possible to mix media with higher density and viscosity. This is particularly advantageous when using the mixing container as a bioreactor. It was found that intensive stirring could be maintained even toward the end of a cultivation procedure, where the cell density has very much increased. In a preferred refinement, this construction makes it possible to operate the central shaft using a plurality of mixing elements, which can be used for more intensive mixing of the container contents and hence for shorter operating times. The use according to the invention of one or more spargers further promotes the stirring by a type of gas/air lifting effect and, when operated as a bioreactor, the simultaneous supply of a culture solution with the required gasses is ensured.

To ensure a high quality of mixing, provision is made for online monitoring of the mixing process or the cultivation by means of sensors or by taking samples. Due to the fact that it is essential to maintain sterile conditions, in particular when using the mixing container in bio-processes, the inlets and outlets of the flexible container are equipped with aseptic connectors and a drain port, which is preferably integrated in the flange, installed at the bottom of the container. As a result of this, the mixing container can be used not only once, but also for a number of successive or even continuous mixing and culture processes without needing to reequip said container, which could endanger the sterile conditions.

Designing the central shaft using shaft elements that can be assembled before operation is particularly advantageous. This is a precondition for folding together the ready-for-use and possibly sterilized mixing container with all preinstalled inner components. This makes it possible to send the complete mixing container to the user with little dead volume. This advantage becomes important in particular when large-volume apparatuses are sent.

BRIEF DESCRIPTION OF THE DRAWINGS

The present invention will be better understood when considered in view of the attached drawings, in which like reference characters indicate like parts. The drawings, however, are presented merely to illustrate the preferred embodiment of the invention without limiting the invention in any manner whatsoever.

FIG. 3A is a perspective view of a portion of a sectioned shaft for use in the mixing vessel of the present invention.

FIG. 3B is a perspective view of a portion of a telescopic shaft for use in the mixing vessel of the present invention.

DETAILED DESCRIPTION OF THE PREFERRED EMBODIMENT

Figure 1:
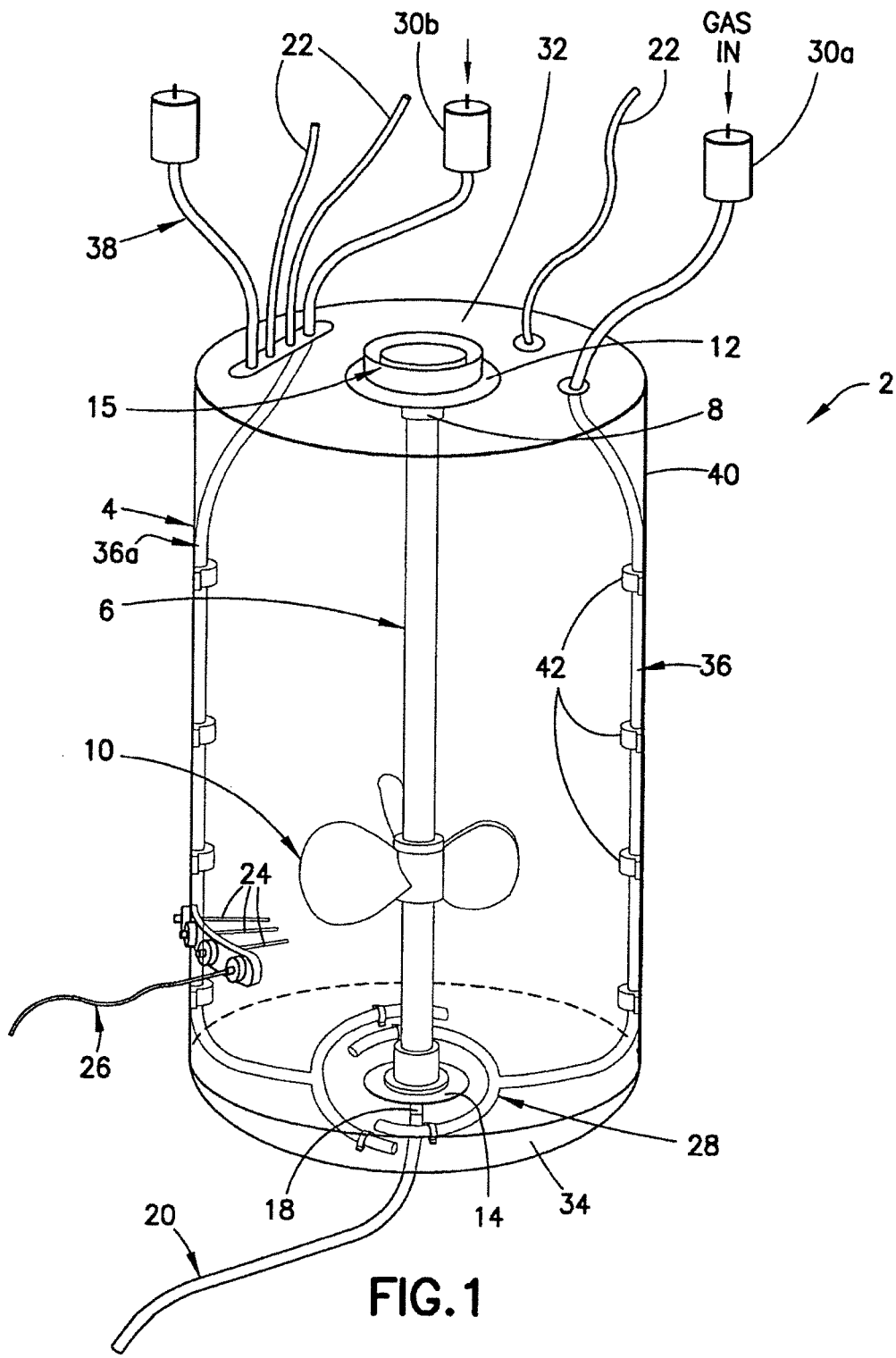
FIG. 1 is a perspective view of the preferred embodiment of the mixing vessel of the present invention.

In one preferred embodiment, as shown in FIG. 1, the disposable mixing vessel 2 of the present invention comprises a flexible container 4 having a centrally disposed shaft 6 with a magnetic element 8 at one end and one or more impellers 10 mounted thereon. The shaft 6 is associated with top and bottom flanges 12 and 14 on the vessel 2, and includes thrust bearings 74 (shown in FIGS. 11A and 11B) between the shaft 6 and one or both of the flanges 12 and 14 for facilitating rotation of the shaft 6. The top flange 12 preferably includes a drive coupling 15 for receiving the magnetic drive element of a drive motor 80 (shown in FIG. 11A). The bottom flange 14 includes a drain port 18 with access to the interior of the vessel 2 for draining the vessel 2, preferably using a harvest line 20 attached to the drain port 18, after the mixing process has been completed.

The mixing vessel 2 includes one or more inlets 22 for filling the vessel 2 with the materials to be mixed. It is preferred that the vessel 2 incorporates one or more sensors 24 across the flexible container 4, for measuring various properties of the materials being mixed in the vessel 2, and/or sampling lines 26, for removing a sample of the material in the vessel 2 for analysis. Preferably, the sensors 24 and sampling lines 26 are located in the bottom third of the mixing vessel 2.

The mixing vessel 2 shown in FIG. 1 includes a sparger 28 for introducing gases into the mixture. To introduce a gas into the vessel 2 one or more gas inlets 30 are preferably located on the top portion 32 of the flexible container 4. The gas inlet 30 can be any fitting through which gas can pass to a sparger line 36 on the interior of the vessel 2, which feeds the sparger 28 preferably located at the bottom of the vessel 2. In the preferred embodiment shown, the sparger 28 is attached to the bottom portion 34 of the container 4 about the bottom flange 14 to improve mixture of the gas with the materials being mixed in the vessel 2. One or more gas exhausts 38 permits the gas that has not been mixed into the materials in the vessel 2 to be removed from the vessel 2, preferably for recycle into the gas inlet 30 as necessary.

The sparger line 36 is preferably a tube or a sleeve that is attached to a side wall 40 of the container 4 to keep the sparger line 36 from interfering with the rotating shaft 6 and the one or more impellers 10 mounted on the rotating shaft 6. The sparger line 36 or sleeve 36' and sparger 28 can be attached to the flexible container 4 by any means, preferably including welding, adhesives or bands or straps 42 that keep the sparger line 36 and sparger 28 properly located within the container 4.

Figure 2A:
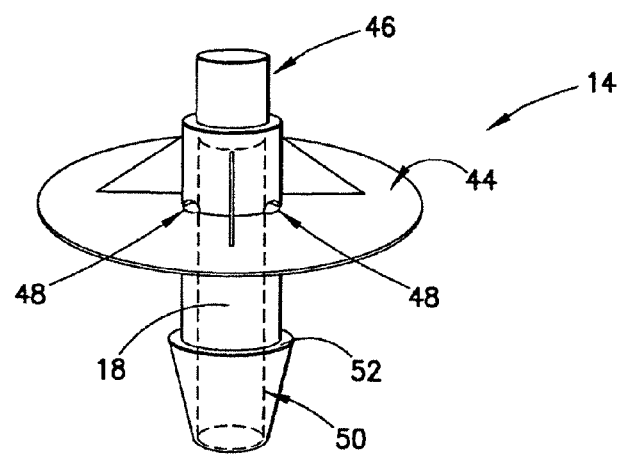
FIG. 2A is a perspective view of a first embodiment of a bottom flange for use as part of the mixing vessel of the present invention.
Figures 2B, 2C:
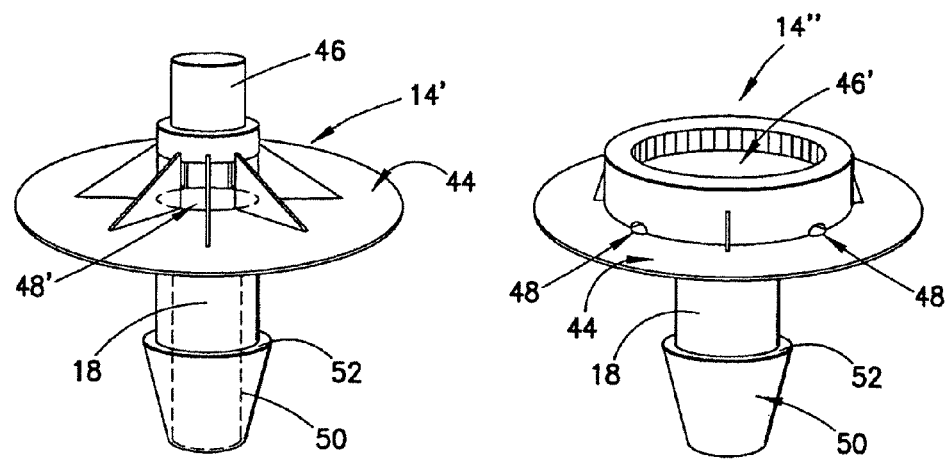
FIG. 2B is a perspective view of a second embodiment of a bottom flange for use as part of the mixing vessel of the present invention.
FIG. 2C is a perspective view of a third embodiment of a bottom flange for use as part of the mixing vessel of the present invention.

The bottom flange 14 associated with the bottom of the shaft 6 and forming part of the vessel 2 is more particularly shown in FIGS. 2A-2C, where several embodiments are illustrated. Each of the bottom flange 14 embodiments are formed of a substantially rigid material, preferably a rigid plastic, and include a flange plate 44 that is connected to the flexible container 4 in the center of the bottom portion 34. The flange plate 44 can be connected to the flexible container 4 in any known way that creates a hermetic seal between the rigid and flexible materials.

The upper portion of the bottom flange 14, which is maintained in the interior of the vessel 2, includes a mating member 46 which engages the bottom of the centrally disposed shaft 6. The mating member 46 can be either a male member 46 as shown in FIGS. 2A and 2B, which is inserted into an opening at the bottom of the shaft 6 (not shown), or a female member 46' into which the bottom terminal end of the shaft 6 is inserted. It is preferred that the shaft 6 fit on the mating member 46 with a minimal friction, so that the shaft 6 can freely rotate on the mating member 46, including the possible inclusion of a thrust bearing (not shown) between the shaft 6 and the mating member 46. If desired, a catch (not shown) that does not significantly impair rotation of the shaft 6 on the mating member 46 can be used to secure the shaft 6 to the mating member 46.

As described above, the bottom flange 14 also includes a drain port 18. The drain port 18 is associated with apertures 48 on the interior portion of the bottom flange 14 for access to the interior of the vessel 2 and removal of the mixture from the vessel 2 after the batch has been fully mixed. The drain port 18 preferably has a barbed tip 50 for receiving the harvest line 20. The barbed tip 50 flares down to a lesser external diameter at the terminal end to facilitate connection of the harvest line 20 and preferably includes a shelf 52 which assists in keeping the harvest line 20 from slipping off of the drain port 18.

To improve packing and storage of the mixing vessel 2 prior to use, the present invention contemplates a shaft 6 that is included in sections within the shipped and/or stored vessel that must be assembled during preparation for receiving the materials to be mixed. This will especially aid in large volume applications of the present technology.

In this embodiment the shaft is formed of sections that can be assembled from a shipped configuration to a mixing configuration.

Various structures and methods for assembling a shaft 6 from sections are contemplated. For example, FIG. 3A shows sections 54 of a shaft 6 that have corresponding threaded ends 56 and 58 where the sections 54 can be screwed together to create the shaft 6. In the embodiment of FIG. 3A, the sections 54 further include a treaded terminal end 56 for receiving the magnetic element 8 that makes up the top of the shaft 6, as more fully described below.

In this embodiment, the sections 54 with threaded terminal ends 56 can be incorporated as separate parts in a space-saving fashion in the flexible container 4 which may be folded flat during shipping. After shipping, the sections 54 can be manually assembled from outside of the flexible container 4 before starting operation of the flexible container 4 in order to create the ready-to-use shaft 6 without disrupting the sterility of the optionally presterilized flexible container 4. Hence, a user may assemble these sections 54 with the preferably flexible walls 40 of the container 4 serving as a sterile barrier between the sections 54 to be manually assembled in the container 4 and the environment, so that the sterility of the interior of the flexible container 4 is maintained.

An alternative to the use of threaded ends 56 and 58 to secure sections 54 of a shaft 6 is the use of telescoping sections 54, where a first section 54 is slidably stored inside of a second section 54'. In this embodiment, the first and second sections 54 and 54' lock with relation to one another when the sections 54 are fully extended. Although any structure for locking the sections 54 and 54' in an open configuration can be used, a spring catch 60 is most preferred. For example, the spring catch 60 can use a living hinge with a detent end or a spring pushing a ball outward on the interior section 54, with the detent or ball engaging a receiving hole on the exterior section 54', as suitable constructions.

In this embodiment, the first section 54 can be slidably stored inside the second section 54' in a space saving fashion in the flexible container 4 which may be folded flat during shipping. After shipping, the sections 54 can be extended from outside the flexible container 4, like a telescope, before starting operation of the flexible container 4 in order to create the ready-to-use telescopic shaft 6 without disrupting the sterility of the optionally presterilized flexible container 4. Hence a user may manually extend these telescopic sections 54, 54' with the preferably flexible walls 40 of the container 4 serving as a sterile barrier between the sections 54, 54' to be manually assembled in the container 4 and the environment, so that the sterility of the interior of the flexible container 4 is maintained.

It is also possible to use more than two sections 54, 54', respectively, to enlarge the shaft 6 to predetermined, variable lengths.

As a result of the telescopic design of the shaft 6 comprising a plurality of segments 54, 54' which can be latched into one another via the device 60, it is possible to increase the length of the shaft 6 during the mixing process in a number of steps without interrupting the sterility limit, so that the shaft length is also automatically adapted to the increased mixing container volume in a manner analogous to an upscale process in the case where the volume in the flexible container 4 is increased sequentially and in a number of steps.

To increase the mixing power, each segment 54 can have an impeller 10 with respectively one collar 64 which can be displaced along the segment 54 and which, by means of the adjacent segment 54', can be locked with the larger diameter adjacent to the device 60 in the telescopically extended state of the shaft 6.

Figure 3E:
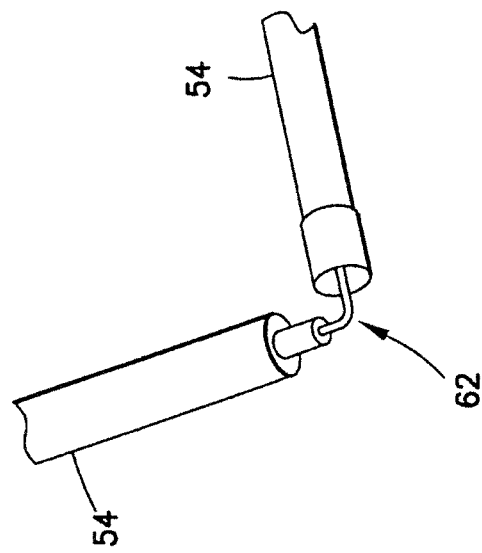
FIG. 3E is a perspective view of a portion of a third embodiment of a jointed shaft for use in the mixing vessel of the present invention.
Figure 3D:
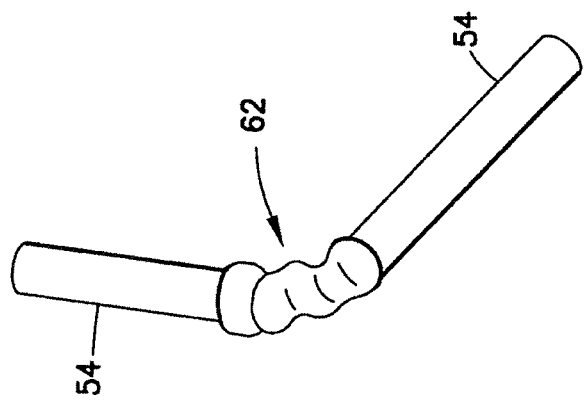
FIG. 3D is a perspective view of a portion of a second embodiment of a jointed shaft for use in the mixing vessel of the present invention.
Figure 3C:
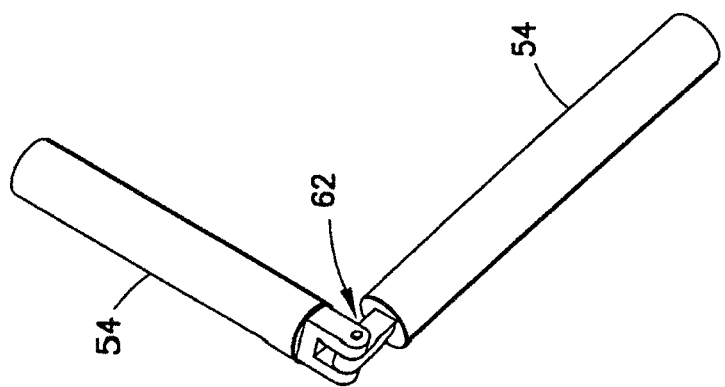
FIG. 3C is a perspective view of a portion of a first embodiment of a jointed shaft for use in the mixing vessel of the present invention.
Figure 4:
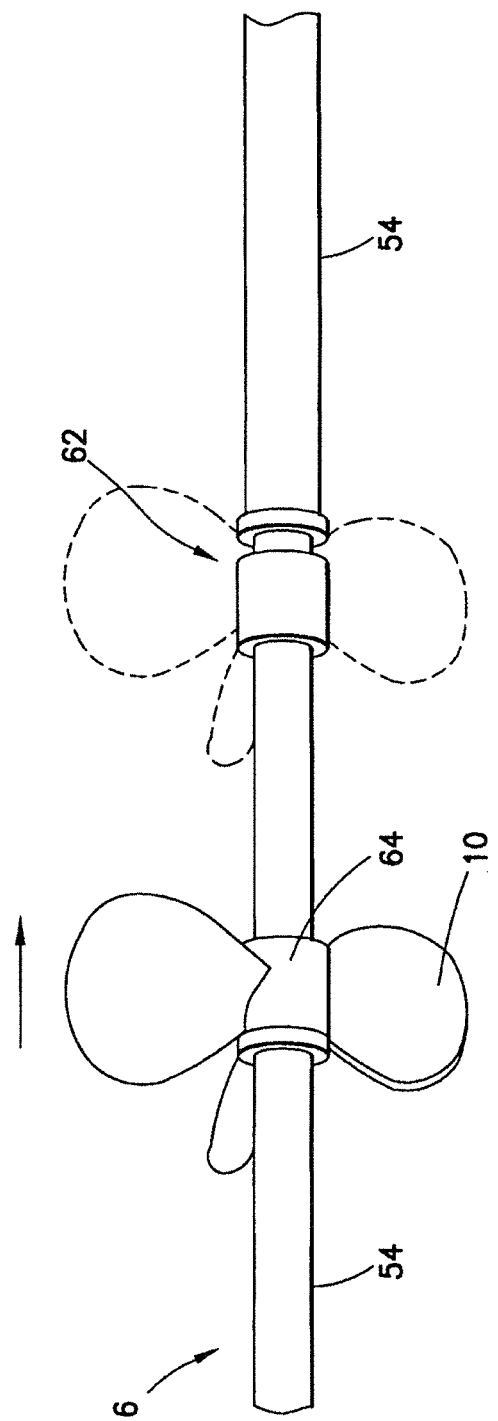
FIG. 4 is a perspective view of a portion of a jointed shaft for use in the mixing vessel of the present invention with an impeller mounted thereon.

Other alternatives for sectioned shafts 6 include the use of hinges 62 that can be manipulated from a folded position to an open position, examples of which are shown in FIGS. 3C-3E. These examples include a hinge 62, shown in FIG. 3C, that pivots in a single plane, as well as flexible elastic hinges 62', shown in FIGS. 3D and 3E, that pivot in a variety of planes. In these, the sections 54 can be maintained in an open configuration through the use of locking hinges, which are lockable in a wide variety of known ways, or by the use of a sleeve 64 that covers the hinge 62 to prevent pivoting. For example, in the embodiment shown in FIG. 4 the impeller 10 is formed with a sleeve 64 for sliding on the shaft 6 to the area covering the hinge 62 to prevent the hinge 62 from pivoting. Preferably, a locking mechanism (not shown) locks the sleeve 64 of the impeller 10 in place over the hinge 62 to ensure that the hinge 62 is maintained in the open configuration.

In this embodiment the sectioned shaft 6 can be folded flat in a space-saving fashion in the flexible container 4 which may be also folded flat during shipping. After shipping, the sectioned shaft 6 can be manually manipulated from outside the flexible container 4 from the folded position to the open position by use of the hinges 62 before starting operation of the flexible container 4 in order to create the ready-to-use unfolded, sectioned shaft 6. Hence, a user may unfold the sectioned shaft 6 via the preferably flexible walls 40 of the flexible container 4 which serve as a sterile barrier ensuring the maintenance of the sterility of the interior of the flexible container 4.

In any embodiment where the shaft 6 is shipped and stored in sections, it is preferred that the sectioned shaft 6 be constructed sterile and hermetically sealed in the mixing vessel 2 for shipping and storage, and that the sections 54 of the shaft 6 be assembled into the open configuration in the mixing vessel 2 without breaching the seal of the vessel 2.

Figure 14:
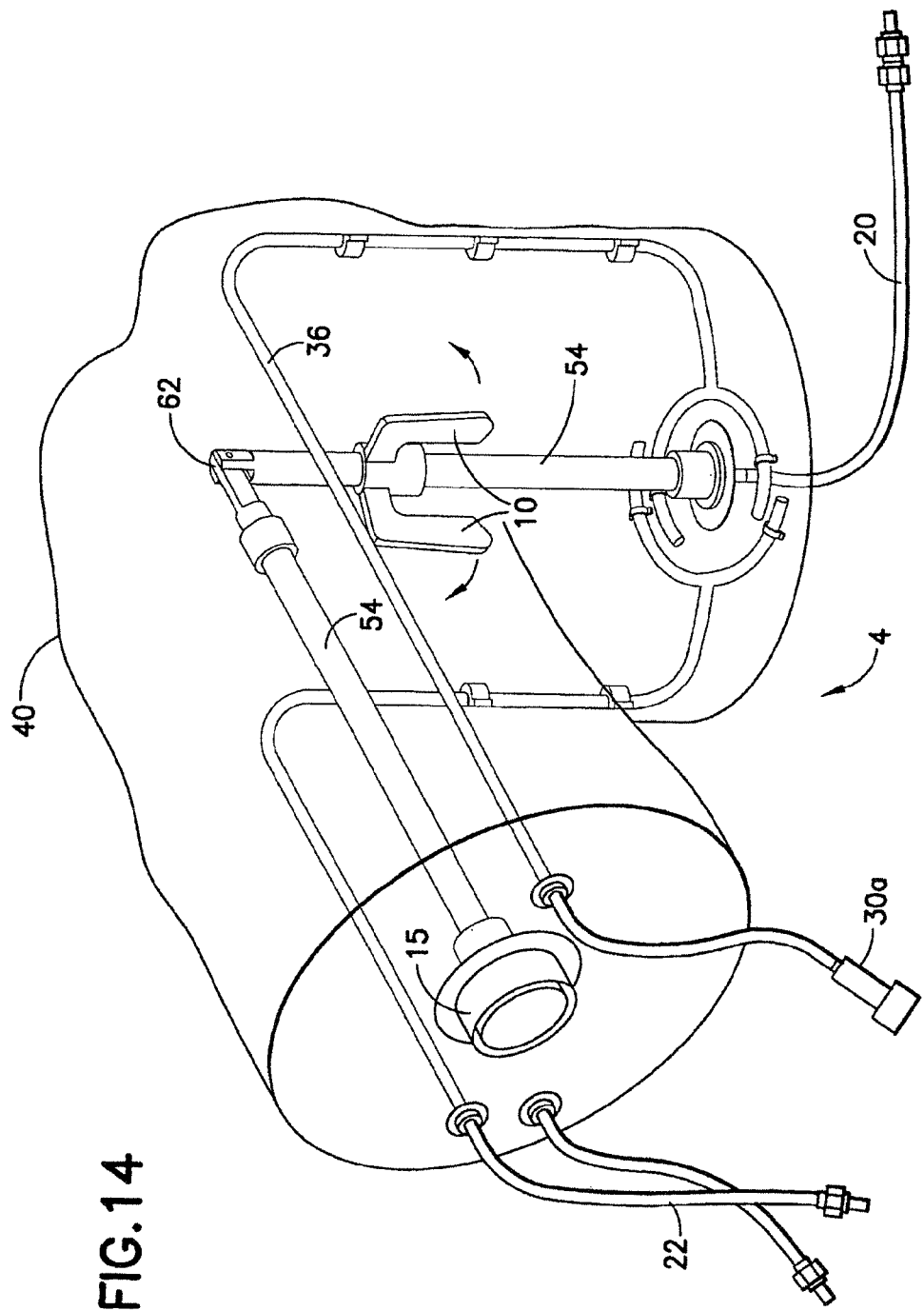
FIG. 14 is a perspective view of another preferred embodiment of the mixing vessel of the present invention in a partially collapsed configuration, prior to full assembly of the shaft and filling with the material to be mixed.

FIG. 14 shows one embodiment of the present invention, where the flexible container 4 has been folded flat in a space saving fashion for purposes of shipping and storage. The flexible container 4 has a foldable shaft 6 which is transformed into its operation configuration by unfolding the flexible container 4 and manually manipulating the sections 54 of the foldable shaft 6 about the hinge 62 from a closed position to an open position from outside the bag without disrupting the integrity and sterility of the flexible container 4. In this embodiment, the impeller 10 has one or more blades that are also foldable during shipping. The impeller 10 may be positioned at a predetermined level on the shaft 6 and the blades of the impeller 10 may be unfolded in an analogous manner as during the assembly of the shaft 6.

The top of the shaft 6 incorporates a magnetic element 8, preferably including a plurality of magnets 66, which is made part of the shaft 6 by any means of attachment or construction. The magnetic element 8 of the shaft 6 is then positioned adjacent the top flange 12 of the vessel 2. A preferred magnetic element 8 and top flange 12 arrangement is shown in FIGS. 9A and 9B, where the magnetic element 8 is connected to the top flange 12 so as to enable the magnetic drive means (not shown) to act upon the magnets 66 of the magnetic element across the top flange 12.

Figure 9A:
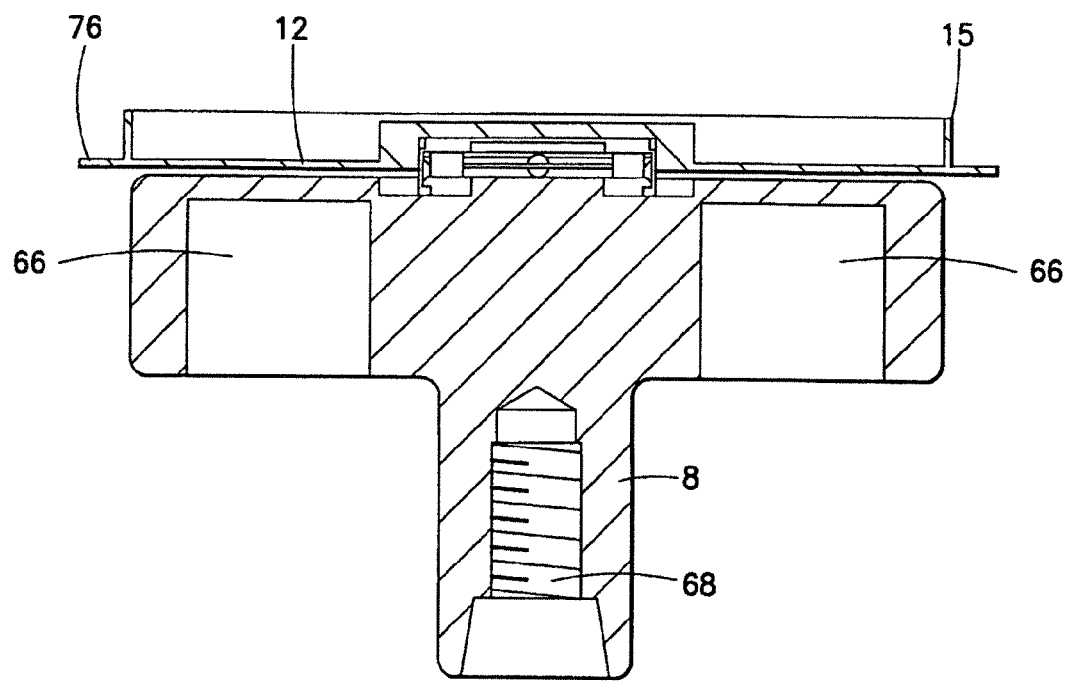
FIG. 9A is a schematic cross section of the top flange and magnetic element of the shaft of the present invention.
Figure 9B:
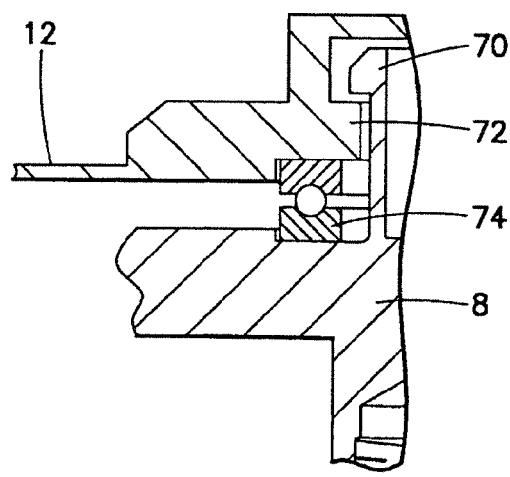
FIG. 9B is a cross section of a portion of a preferred connection between the top flange and the magnetic element of the shaft of the present invention.

In the embodiment of FIG. 9A the magnetic element 8 is fixed on the shaft 6 by screwing a threaded end 56 of the shaft 6, as shown in FIG. 3A, into a threaded opening 68 within the magnetic element 8. Of course, other means such as keyed members, adhesives, clips, snaps, pins, screws, latches, welding, and the like, as well as forming the magnetic element 8 on the shaft 6 during construction of the shaft 6, can be used to attach the magnetic element 8 to the shaft 6, without limitation.

To keep the magnetic element 8 in proper relation to the top flange 12, the preferred embodiment of the present invention includes a hook or catch 70 on the magnetic element 8 that engages a lip 72 on the top flange 12. Of course, the particular means for attaching the magnetic element 8 and the top flange 8 is not essential, including not only the use of the catch 70 associated with the top flange 12 and the lip 72 associated with the magnetic element 8, but alternatives such as snaps, channels and the like are contemplated, as long as the magnetic element 8 can rotate relatively freely in relation to the top flange 12. To assist in the free rotation of the magnetic element 8 in relation to the top flange 12, the use of thrust bearings 74 between the magnetic element 8 and the top flange 12 is contemplated.

Additionally, to ensure that the magnetic drive means (not shown) maintains proper alignment with the magnets 66 of the magnetic element 8, the top flange 12 preferably includes a drive coupling 15 that extends upwardly from the exterior surface of the top flange 12. As with the bottom flange 14, the top flange 12 is formed of a rigid material, including a rigid plate 76 for connection to the flexible container 4 with a hermetic seal.

Figure 5:
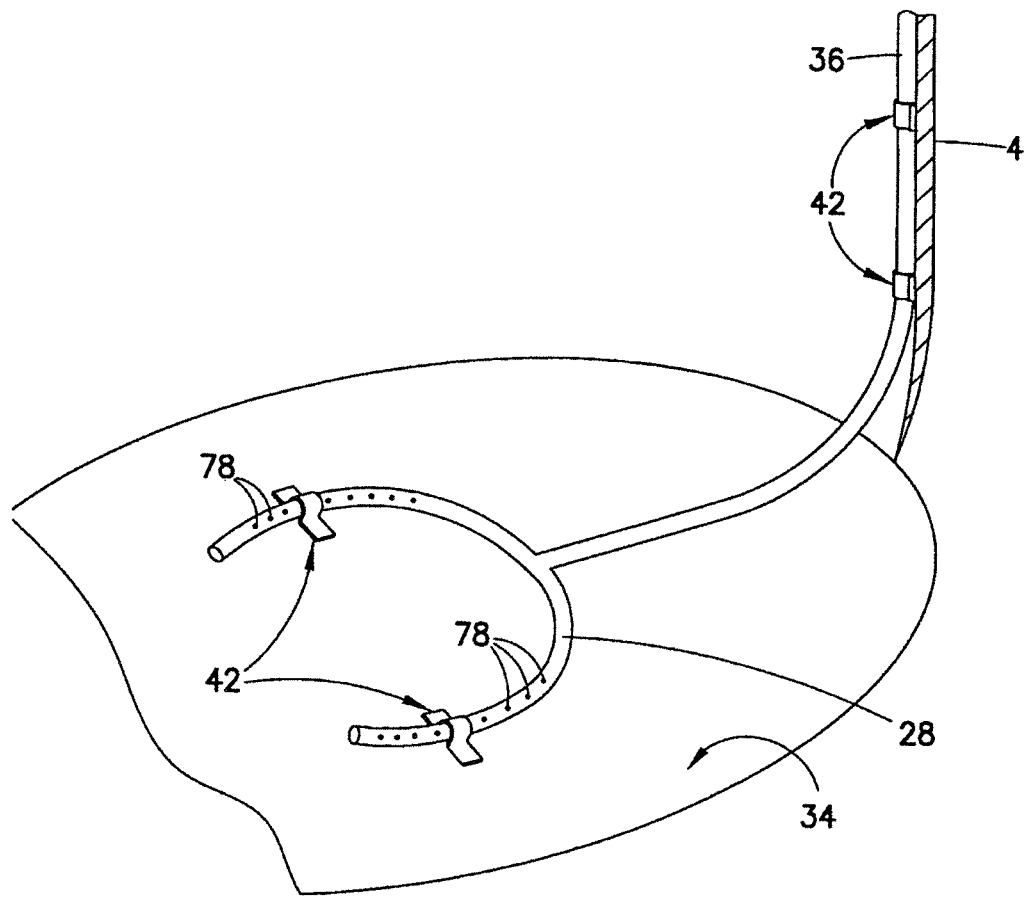
FIG. 5 is a perspective view of a preferred sparger with a tubular feed line for use in the mixing vessel of the present invention.

The sparger 28, having holes 78 for releasing gas into the mixture, is more particularly shown in FIGS. 5. The sparger 28 is preferably attached to the flexible container 4 with flexible straps 42 welded to the interior of the bottom portion 34 of the flexible container 4. Of course, other means for attaching the sparger 28 may be used, including adhesives, clips, and the like, however, welding straps 42 formed of the same material as the interior of the flexible container 4 to the interior of the flexible container 4 is most preferred.

Figure 6:
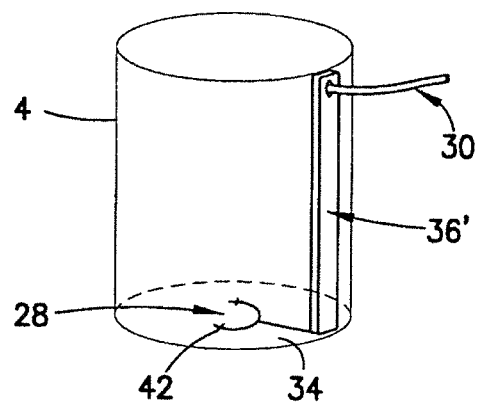
FIG. 6 is a perspective view of a sparger with a sleeve feed line for use in the mixing vessel of the present invention.
Figure 7A:
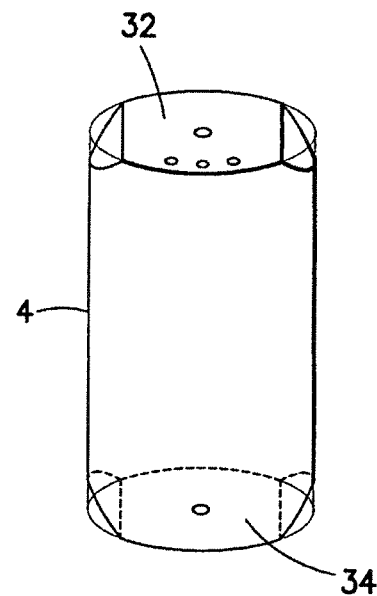
FIG. 7A is a perspective view of a first embodiment of the flexible portion of the mixing container of the present invention.
Figure 7B:
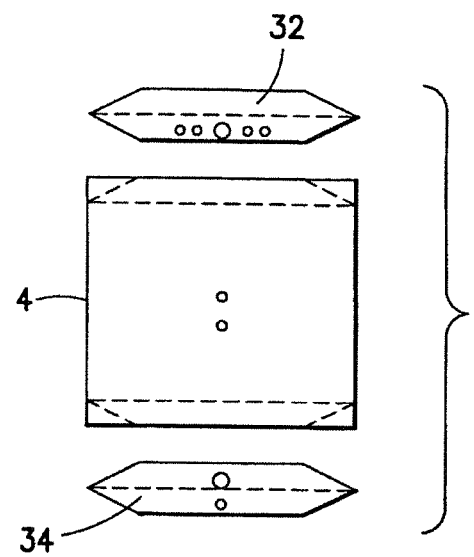
FIG. 7B is a plan view of a first embodiment of the flexible portion of the mixing container of the present invention in the folded and open configurations.
Figure 8A:
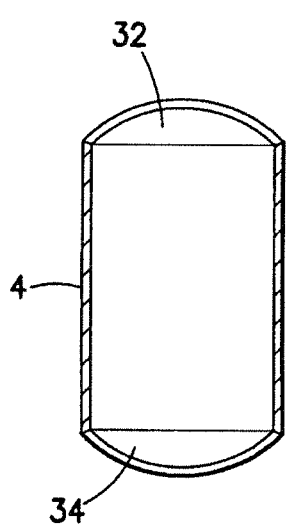
FIG. 8A is a perspective view of a second embodiment of the flexible portion of the mixing container of the present invention.
Figure 8B:
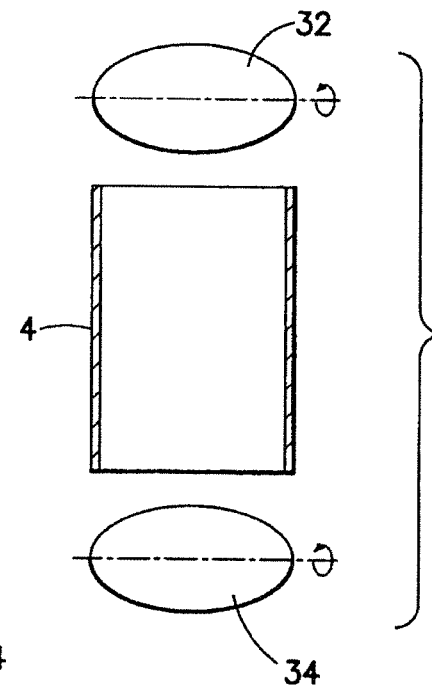
FIG. 8B is an elevational view of a second embodiment of the flexible portion of the mixing container of the present invention in its open configuration.
Figure 8C:
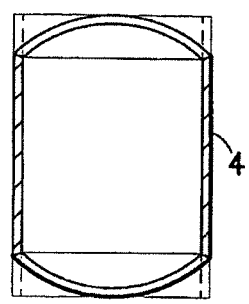
FIG. 8C is an elevational view of a second embodiment of the flexible portion of the mixing container of the present invention in its folded configuration.

An alternative construction for the sparger line 36 is shown in FIG. 6, which uses a sleeve 36' as the sparger line. In this embodiment, the sleeve 36 is constructed of a length of material, preferably the same as the interior of the flexible container 4, welded or otherwise affixed at the longitudinal sides to the interior of the flexible container 4. The area between the sleeve 36' and the flexible container 4 carries the gas from the gas inlet 30 to the sparger 28.

Figure 12:
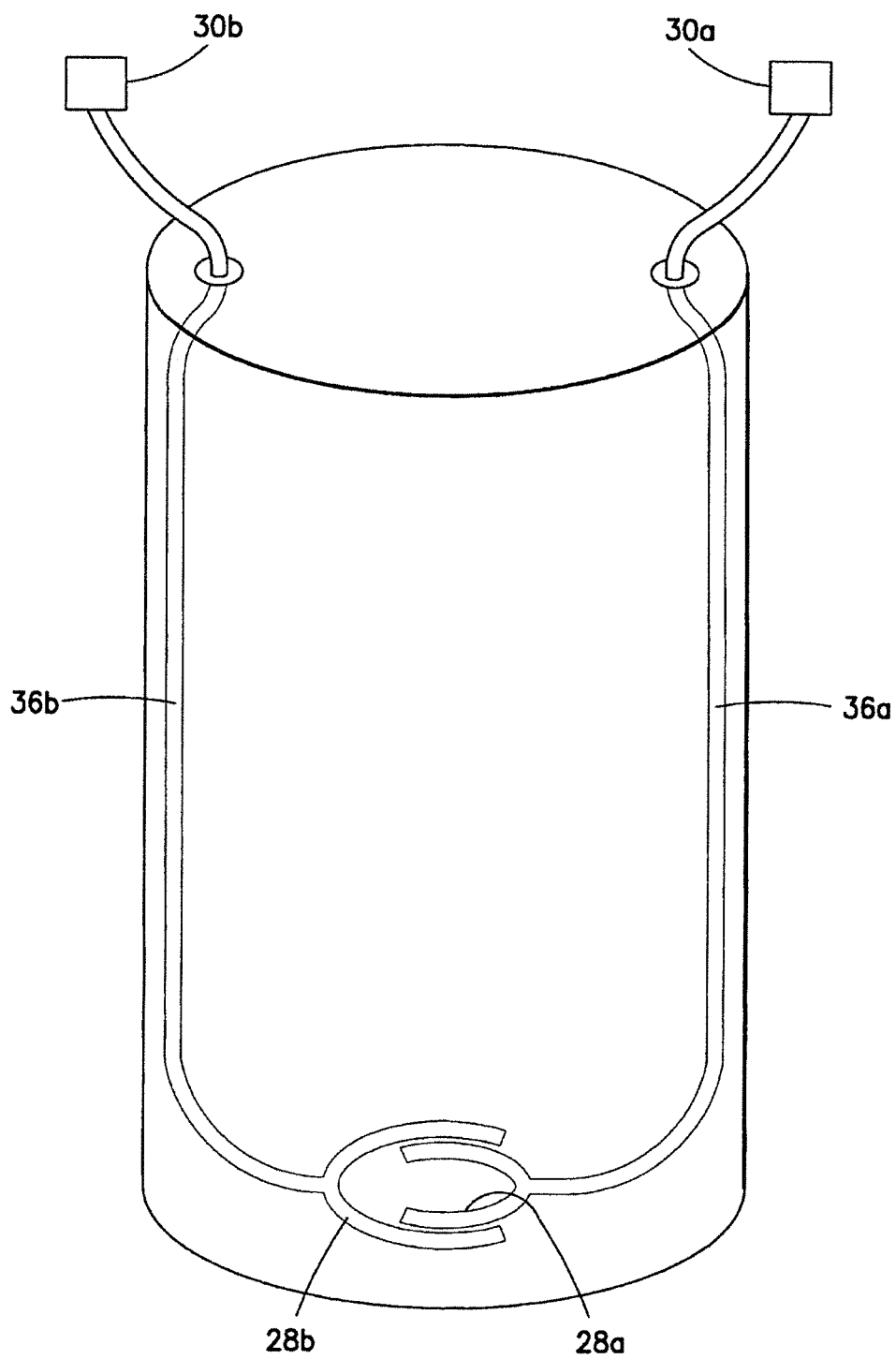
FIG. 12 is an alternative embodiment of the flexible vessel of the present invention with two spargers.

In the event that the process calls for sparging more than one gas into the mixture, the mixing vessel 2 may have more than one sparger 28. For example, if both $O_2$ and $CO_2$ are to be introduced to the mixture it is contemplated that the mixing vessel 2 may have two spargers 28a and 28b, as shown in FIG. 12. When using two spargers 28a and 28b for different gasses, different sparger lines 36a and 36b, fed by different gas inlets 30a and 30b could be used.

Moreover, the different spargers 28a and 28b can have different characteristics related to the type or volume of gas that is being introduced into the mixture. These different characteristics can include, but are not limited to the size and number of the holes (not shown). Additionally, the two spargers 28a and 28b can be incorporated into the mixing vessel 2 in any manner, with each being incorporated the same or different ways, as a manner of design choice.

When using at least two spargers 28, it was a surprise to find that the sparger lines 36, which lie on the wall 40 as protrusions which extend into the inside of the flexible container 4, simultaneously act as flow breakers/baffles, which further increase the stirring of the mixing container contents in the flexible container 4. The parallel arrangement of at least three and preferably four spargers 28 with equidistant spacing on the wall 40 is particularly preferred in order to optimally use this flow breaking effect of the sparger lines 36.

As stated above, the flexible container 4 of the mixing vessel 2 can have any suitable shape, however, the shape must be determined with considerations to eliminating areas where flow of the materials may be reduced, folding the mixing vessel 2 for shipping and storage, and unfolding of the vessel 2 for use. FIGS. 7A, 7B and 8A-8C show various configurations of the flexible container 4 that are considered to be suitable for use with the present invention, without limitation.

In one embodiment of the present invention, the shape of the flexible container 4 is preferably hemispherical, allowing for more efficient mixing and sparging of its contents.

Figure 13:
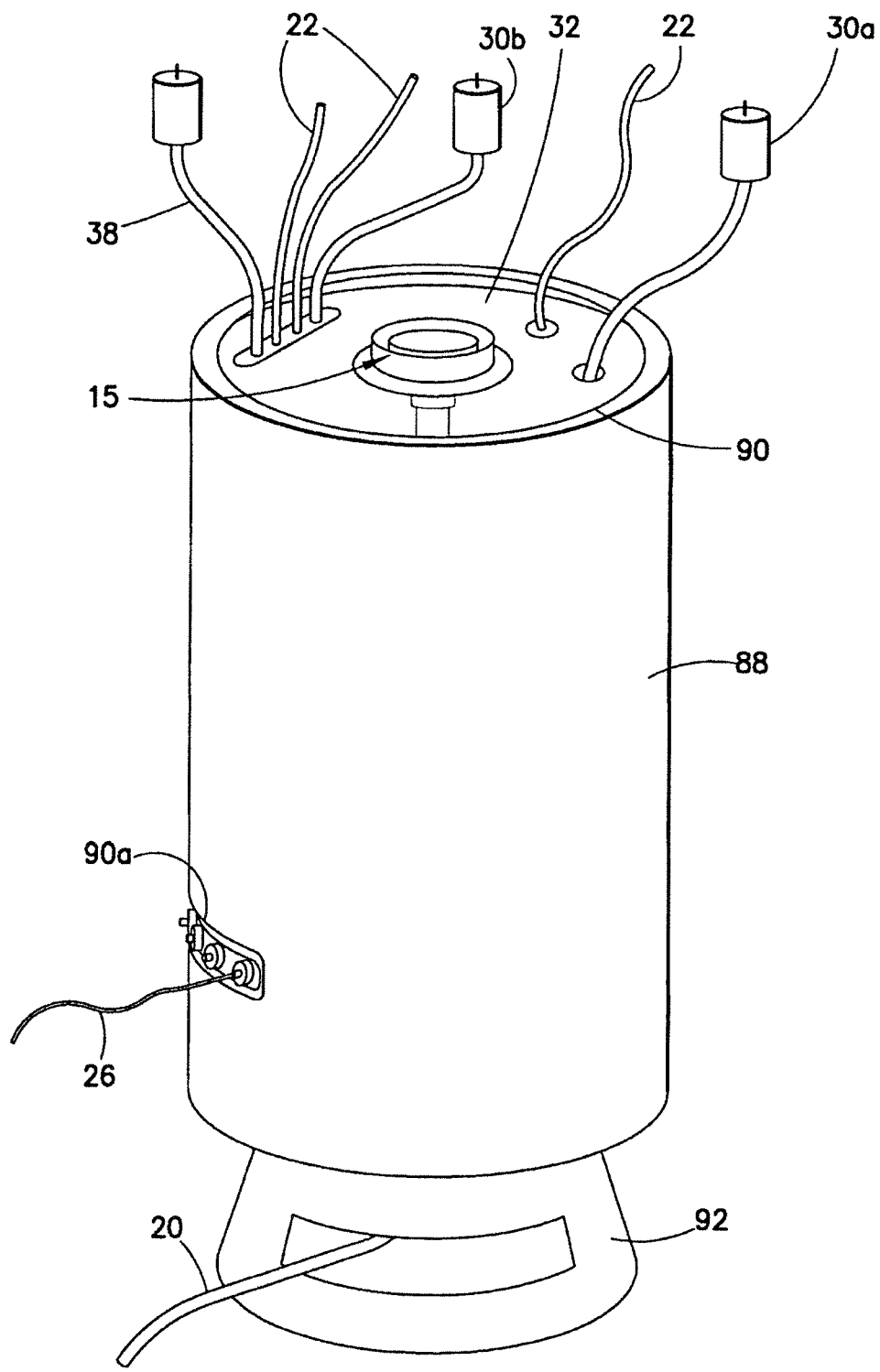
FIG. 13 is a partial cross section of the flexible vessel shown in a rigid or semi-rigid tank of generally the same geometry, size and shape to maintain the integrity of the flexible container.

Due to the flexible nature of the container 4, the mixing vessel 2 is preferably supported by a rigid or semi rigid container or tank 88 during filling, mixing and draining The preferred tank 88 is of generally the same geometry, shape and/or size as the flexible container 4, and is preferably hemispherical, to minimize stress at seams or changes of direction in the material of the flexible container 4 (see FIG. 13).

Notwithstanding, the tank 88 would have one or more openings 90, 90a for inserting the empty mixing vessel 2 prior to use and accessing the various elements that need to be accessed during use of the mixing vessel 2, including the drive means 15, inlets 22, exhaust 38, sampling lines 26, etc. Similarly, the tank 88 should have legs or a stand 92 to maintain the tank in an upright position while allowing access to the drain port 18 for draining the mixture through harvest line 20.

In a preferred embodiment of the invention, the top and/or bottom of the shaft is rotational by means of radial bearings, such as friction (sliding), journal, ball or roller bearings, and more preferably sliding bearings, similar to that shown in FIG. 9B. In this regard, it is important for efficient mixing that the friction of the shaft being rotated is minimized.

Figure 10:
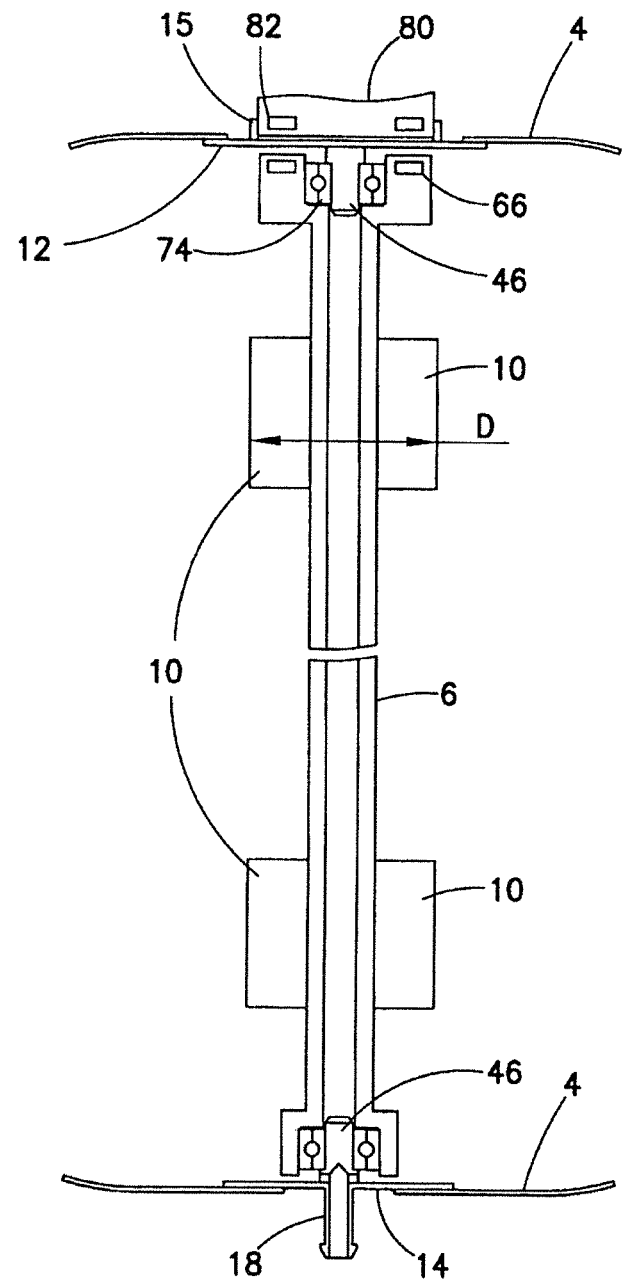
FIG. 10 is a partial cross section of a preferred embodiment of the present invention.
Figure 11A:
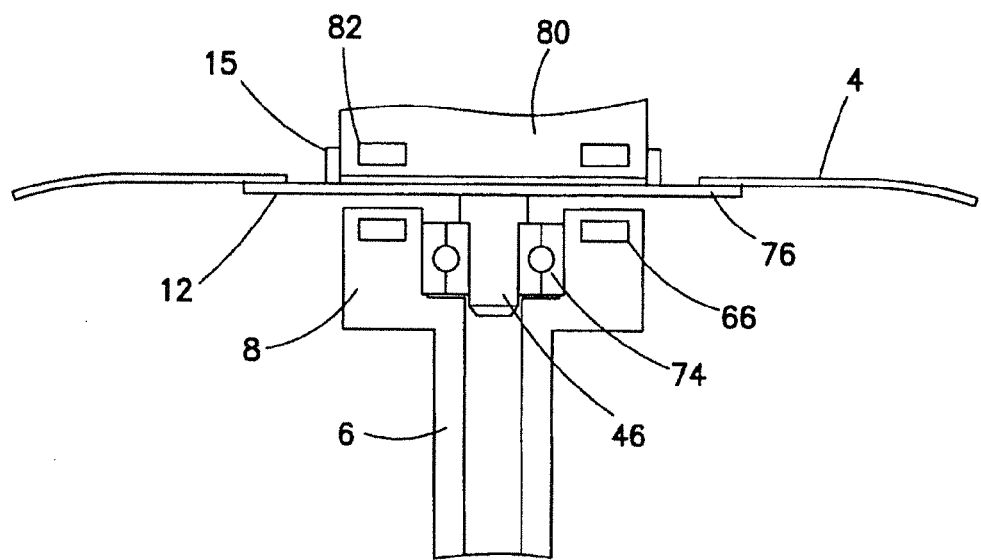
FIG. 11A is a partial cross section of the area of the top flange plate of the preferred embodiment of the present invention shown in FIG. 10.
Figure 11B:
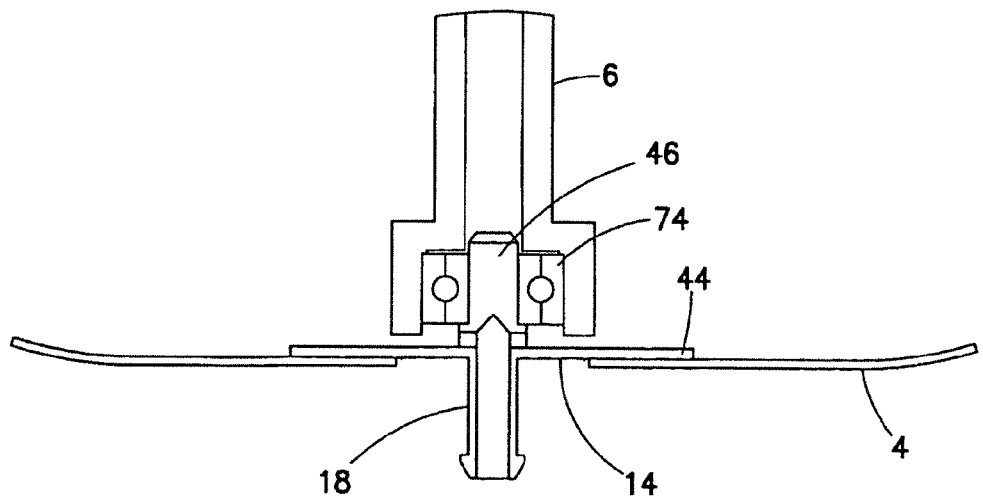
FIG. 11B is a partial cross section of the area of the bottom flange plate of the preferred embodiment of the present invention shown in FIG. 10.

A preferred commercial embodiment of the present invention is shown in FIGS. 10, 11A and 11B. This embodiment includes the elements described above, including the center shaft 6 having impellers 10 thereon, mounted on a top flange 12 and a bottom flange 14 that is hermetically sealed to a flexible container 4. Although not shown, a sectioned shaft 6, sparger 28, material inlets 22, gas inlet 30 and exhaust 38, sensors 24, sampling line 26, harvest line 20 and the like are envisioned for use with this embodiment, as desired and without limitation.

The top flange 12, shown in FIGS. 10 and 11A having a drive motor 80 positioned within the drive coupling 15 so as to orient the drive magnets 82 with the driven magnets 66, includes a mating member 46 as described above with respect to the bottom flange 14. In this embodiment, the thrust bearings 74 are preferably oriented vertically between the mating member 46 of the top flange 12 and the top of the shaft 6. Moreover, the magnet element 8 of this embodiment is preferably formed on the terminal end of the shaft 6, so as to create an integral shaft 6 if desired.

The bottom flange 14, shown in FIGS. 10 and 11B, can include any acceptable mating member 46 with thrust bearings 74 located between the mating member 46 and a portion of the bottom of the shaft 6. Preferably, this includes a lower portion of the shaft 6 being formed as a receiver for the mating member 46 with the trust bearings 74 therebetween. Alternatively, the bottom flange 14 can be formed with a female mating member 46' which receives the shaft 6, with the thrust bearings 74 positioned therebetween. In this embodiment, the trust bearings 74 associated with the bottom of the shaft 6 are also preferably, but not necessarily, oriented vertically.

Variations, modifications and alterations to the preferred embodiment of the present invention described above will make themselves apparent to those skilled in the art. All such changes are intended to fall within the spirit and scope of the present invention, limited solely by the appended claims. All cited prior art is incorporated by reference.

What is claimed is:
1. A disposable mixing vessel comprising:
 a. a flexible container;
 b. a centrally disposed shaft having first and second ends, at least one impeller and a magnetic element associated with a first shaft end;
 c. a first flange adapted to rotatably engage the first shaft end; and
 d. a second flange adapted to rotatably engage the second shaft end.

2. The disposable mixing vessel as defined in claim 1 further comprising bearings located between at least one of the first shaft end and first flange and the second shaft end and second flange.

3. The disposable mixing vessel as defined in claim 1 wherein the second flange comprises a drain port.

4. The disposable mixing vessel as defined in claim 1 further comprising a sparger at the bottom of the container.

5. The disposable mixing vessel as defined in claim 4 wherein the sparger surrounds at least a portion of the second flange.

6. The disposable mixing vessel as defined in claim 4 comprising a second sparger at the bottom of the container.

7. The disposable mixing vessel as defined in claim 6 wherein the second sparger surrounds at least a portion of the second flange.

8. The disposable mixing vessel as defined in claim 4 wherein the sparger is fed by a sparger feed line attached to an inside side wall of the flexible container.

9. The disposable mixing vessel as defined in claim 1 wherein the shaft is formed of sections that can be assembled from a shipped configuration to a mixing configuration.

10. The disposable mixing vessel as defined in claim 9 wherein the shaft is formed of sections that can be assembled from a shipped configuration to a mixing configuration by telescopically extending the sections.

11. The disposable mixing vessel as defined in claim 9 wherein the shaft is formed of sections that can be assembled from a shipped configuration to a mixing configuration by manipulating the shaft from a folded position to an open position.

12. The disposable mixing vessel as defined in claim 9 wherein the shaft is formed of sections that can be screwed together.

13. The disposable mixing vessel as defined in claim 1 further comprising a drive coupling for rotating the shaft.

14. The disposable mixing vessel as defined in claim 13 wherein the drive coupling is adapted to be associated with the first flange.

15. The disposable mixing vessel as defined in claim 1 wherein the flexible container is adapted to be fitted within a rigid or semi-rigid tank.

16. The disposable mixing vessel as defined in claim 1 which can be adapted to a substantially flat folded configuration.

17. The disposable mixing vessel as defined in claim 1 further comprising one or more additional inlets for adding ingredients to the mixture.

18. The disposable mixing vessel as defined in claim 1 further comprising one or more sampling lines for sampling the mixture during mixing.

19. The disposable mixing vessel as defined in claim 18 wherein at least one of the one or more sampling lines is located in the bottom third of the mixing vessel.

20. The disposable mixing vessel as defined in claim 1 further comprising one or more sensors for monitoring variables in the mixing vessel.

21. The disposable mixing vessel as defined in claim 20 wherein at least one of the one or more sensors is located in the bottom third of the mixing vessel.

22. The disposable mixing vessel as defined in claim 3 further comprising a harvest line adapted to be attached to the drain port.

23. The disposable mixing vessel as defined in claim 1 wherein the flexible mixing vessel is formed in a cylindrical shape with a hemispherical top and bottom.

24. A disposable mixing vessel comprising:
  a. a flexible container;
  b. a centrally disposed shaft having first and second ends, at least one impeller and a magnetic element associated with a first shaft end;
  c. a first flange adapted to rotatably engage the first shaft end;
  d. a second flange adapted to rotatably engage the second shaft end;
  e. a drain port; and
  f. at least one sparger.

25. The disposable mixing vessel as defined in claim 24 wherein the second flange comprises the drain port.

26. The disposable mixing vessel as defined in claim 24 comprising two spargers.

27. The disposable mixing vessel as defined in claim 26, wherein oxygen is introduced to the mixing vessel via the first of the two spargers and carbon dioxide is introduced to the mixing vessel via the second of the two spargers.

28. The disposable mixing vessel as defined in claim 26 wherein the two spargers each have holes of different size and/or a different number of holes.

29. A disposable mixing vessel comprising:
  a. a flexible container;
  b. a centrally disposed shaft having first and second ends, at least one impeller and a magnetic element associated with a first shaft end;
  c. a first flange adapted to rotatably engage the first shaft end;
  d. a second flange adapted to rotatably engage the second shaft end; and
  e. at least one sparger.

30. The disposable mixing vessel as defined in claim 29, comprising two spargers.

31. The disposable mixing vessel as defined in claim 30, wherein oxygen is introduced to the mixing vessel via the first of the two spargers and carbon dioxide is introduced to the mixing vessel via the second of the two spargers.

32. The disposable mixing vessel as defined in claim 30 wherein the two spargers each have holes of different size and/or a different number of holes.

33. The disposable mixing vessel as defined in claim 29 further comprising a drain port.

34. The disposable mixing vessel as defined in claim 33 wherein the second flange comprises the drain port.

* * * * *